(12) United States Patent
Mittleman et al.

(10) Patent No.: US 6,665,075 B2
(45) Date of Patent: Dec. 16, 2003

(54) INTERFEROMETRIC IMAGING SYSTEM AND METHOD

(75) Inventors: Daniel M. Mittleman, Houston, TX (US); Jon L. Johnson, Plano, TX (US)

(73) Assignee: WM. Marshurice University, Houston, TX (US)

( * ) Notice: Subject to any disclaimer, the term of this patent is extended or adjusted under 35 U.S.C. 154(b) by 224 days.

(21) Appl. No.: 10/007,983

(22) Filed: Nov. 13, 2001

(65) Prior Publication Data

US 2002/0085209 A1 Jul. 4, 2002

Related U.S. Application Data

(60) Provisional application No. 60/248,444, filed on Nov. 14, 2000.

(51) Int. Cl.⁷ ................................. G01B 9/02
(52) U.S. Cl. ........................ 356/450; 356/456
(58) Field of Search ................ 356/450, 451, 356/456, 497, 512

(56) References Cited

U.S. PATENT DOCUMENTS

| | | |
|---|---|---|
| 5,489,984 A | 2/1996 | Hariharan et al. |
| 5,538,898 A | 7/1996 | Wickramasinghe et al. |
| 5,585,913 A | 12/1996 | Hariharan et al. |
| 5,623,145 A | 4/1997 | Nuss |
| 5,710,430 A | 1/1998 | Nuss |
| 5,729,017 A | 3/1998 | Brener et al. |
| 5,789,750 A | 8/1998 | Nuss |
| 5,877,860 A | 3/1999 | Borden |
| 5,894,125 A | 4/1999 | Brener et al. |
| 5,939,721 A | 8/1999 | Jacobsen et al. |
| 6,078,047 A | 6/2000 | Mittleman et al. |
| 6,414,473 B1 * | 7/2002 | Zhang et al. .......... 324/96 |

OTHER PUBLICATIONS

Z. G. Lu et al.; *Free–Space Electro–Optic Sampling With a High–Repetition–Rate Regenerative Amplified Laser*; (3 p.); American Institute of Physics; Aug. 1997. Only p. 593–595.

T. van Kessel et al.; *Measurement of Trench Depth by Infrared Interferometry*; Optics Letters, vol. 24, No. 23; (3 p.); Dec. 1, 1999. Only p. 1702–1704.

Max Born and Emil Wolf; *Principles of Optics, 7th (expanded) edition*; (Chapters 7 (125 p.) and 10 (79 p.)); 1999. Only p. 286–411 and 554–632.

* cited by examiner

*Primary Examiner*—Samuel A. Turner
(74) *Attorney, Agent, or Firm*—Conley Rose, P.C.

(57) ABSTRACT

A broadband imaging system is disclosed that provides greatly enhanced depth resolution through the use of phase shift interferometry. The system may comprise a transmitter, a splitter, a phase inverter, and a receiver. The transmitter transmits a signal pulse that is split into a measurement pulse and a reference pulse. The measurement pulse is applied to a sample, and a relative phase shift of approximately π radians is introduced between the measurement pulse and the reference pulse by the phase inverter. The measurement and reference pulses are then recombined to form a combined pulse that is detected by the receiver. The phase inverter may be a simple lens that introduces a Gouy phase shift by passing the measurement or reference pulse through a focal point. In this manner, a background-free measurement is provided, which provides a greatly enhanced sensitivity to small changes in the measurement waveform, regardless of origin.

24 Claims, 6 Drawing Sheets

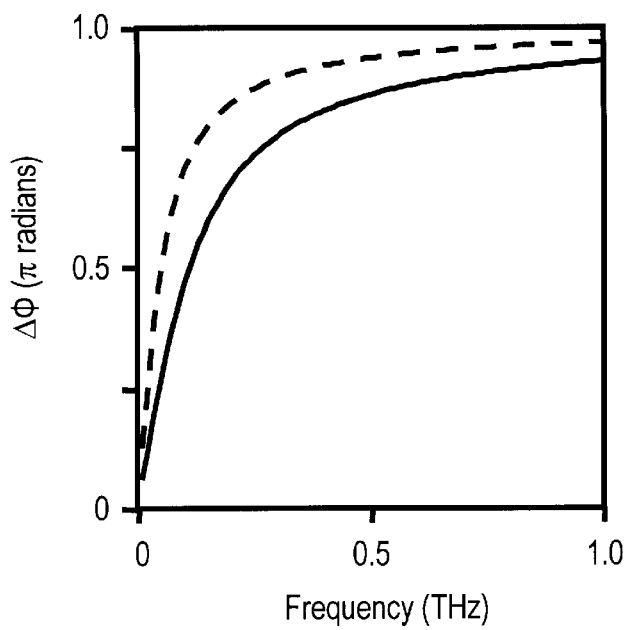
FIG. 1
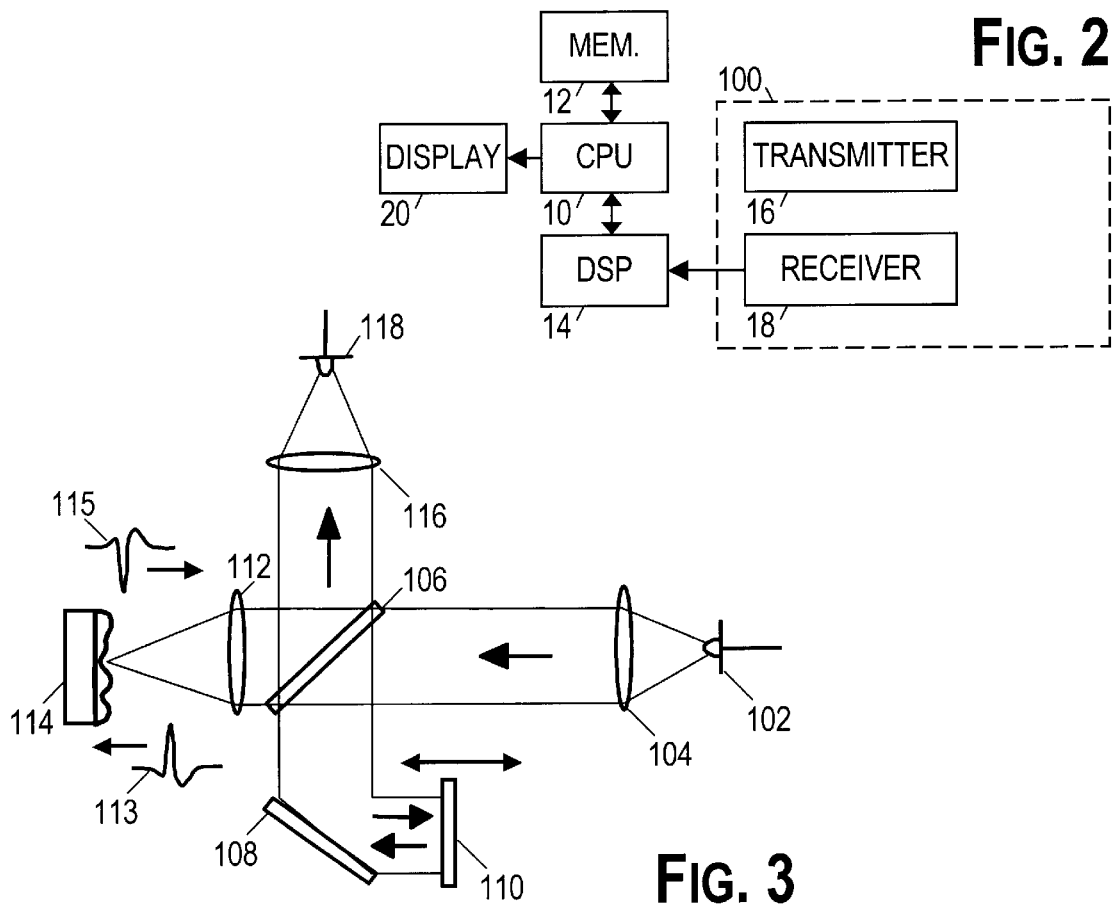
FIG. 2
FIG. 3

INTERFEROMETRIC IMAGING SYSTEM AND METHOD

CROSS-REFERENCE TO RELATED APPLICATIONS

The present application claims priority to a U.S. Provisional Patent Application No. 60/248,444, entitled "Enhanced Depth Resolution Using Interferometric Phase-Shifting Imaging" and filed Nov. 14, 2000, by inventors Daniel M. Mittleman and Jon L. Johnson.

STATEMENT REGARDING FEDERALLY SPONSORED RESEARCH OR DEVELOPMENT

The invention described herein was made in the performance of work under three government grants: two National Science Foundation grants (grant nos. DMR-9802743, ECS-9904264), and an Environmental Protection Agency grant (grant no. R827122-01-1). Accordingly, this invention is subject to Public Law 96-517 (35 U.S.C. §200 et seq.). The contractor has elected to retain title to the invention. Nevertheless, these federal agencies have a nonexclusive, nontransferable, irrevocable, paid-up license to practice or have practiced for or on behalf of the United States the subject invention throughout the world.

BACKGROUND OF THE INVENTION

1. Field of the Invention

This invention generally relates to systems and methods that provide high-resolution imaging of closely spaced interfaces. More specifically, this invention relates to an interferometric imaging system that substantially increases depth resolution relative to non-interferometric systems.

2. Description of the Related Art

Imaging via time-of-flight tomography is common in many fields of research. It is used in optical coherence tomography (OCT), which has found widespread applications, in part because of the ability to image with high depth resolution. In OCT, for example, this resolution is achieved by using a low-coherence light source, such as a femtosecond optical pulse. See M. R. Hee, J. A. Izatt, E. A. Swanson, and J. G. Fujimoto, "Femtosecond transillumination tomography in thick tissues," Opt. Lett., vol. 18, pp. 1107–1109, 1993. In this case, the depth resolution is determined solely by the bandwidth of the light source. This is a manifestation of the well-known Rayleigh criterion, which relates the achievable depth resolution to the coherence length $L_c$, which is inversely proportional to the bandwidth. See Y. Pan, R. Birngruber, J. Rosperich, and R. Engelhardt, "Low-coherence optical tomography in turbid tissue: theoretical analysis," Appl. Opt., vol. 34, pp. 6564–6574, 1995. Using broadband optical pulses of 10 femtosecond duration, it is possible to resolve two reflecting surfaces spaced by only a few microns. See D. Huang, J. Wang, C. P. Lin, C. A. Puliafito, and J. G. Fujimoto, "Micron-resolution of cornea anterior chamber by optical reflectometry," Lasers in Surgery & Medicine, vol. 11, pp. 419–425, 1991. To achieve this extraordinary resolution, an arrangement that provides a synchronized reference pulse for a temporal gate is typically employed.

Terahetz (THz) imaging is a rapidly maturing field. Terahertz systems known as terahertz time-domain spectrometers (THz-TDS) often use laser pulses each lasting only 100 femtoseconds (one tenth of a trillionth of a second) to generate, detect, and measure electromagnetic pulses ("T-rays") that each last for about a picosecond (a trillionth of a second, or $10^{-12}$s). T-rays can be transmitted through various objects, using an imaging system of lenses and mirrors to focus the T-rays. As the T-rays pass through the object under test, they are typically distorted. These changes in the T-ray signals can be analyzed to determine properties of the object. Materials can be characterized by measuring the amounts of distortion—from absorption, dispersion and reflection—of the T-rays passing through to a detector. A digital signal processing unit processes the data and translates it into images that appear on a computer screen. The digital signal processor can be programmed to recognize the characteristic shapes of transmitted waveforms and identify the particular material at the spot illuminated by the T-ray beam. This information can be obtained for every point or "pixel" on each object.

Because many compounds change T-rays in characteristic ways (e.g., absorption or dispersion), molecules and chemical compounds (particularly in the gas phase), show strong absorption lines that can serve as "fingerprints" of the molecules. T-ray imaging can distinguish between different chemical compositions inside a material even when the object looks uniform in visible light. Although metals and other materials with high electrical conductivity are completely opaque to terahertz radiation, most plastics are transparent to T-rays, so THz systems can "see" inside plastic packaging. Many applications of terahertz imaging have been identified, including package inspection, quality control, and gas sensing. One specific application is the semiconductor industry, where detection of very thin or subtle features in packaged integrated circuits is often desired.

In previous work, single-cycle pulses of terahertz radiation have been used for reflection imaging. Because the imaging is performed with short pulses, a three-dimensional image of the object under study can be obtained using a time-of-flight mode. See D. M. Mittleman, S. Hunsche, L. Boivin, and M. C. Nuss, "T-ray tomography," Opt. Lett., vol. 22, pp. 904–906, 1997. Pulses reflected from spatially separated surfaces in the object arrive at the detector at different times. The time delay between adjacent pulses can be related to the distance between the two reflecting surfaces.

One of the unique aspects of the technique of THz-TDS is that it is based on photoconductive or electro-optic sampling, which permits the direct detection of the THz electric field. See P. R. Smith, D. H. Auston, and M. C. Nuss, "Subpicosecond photoconducting dipole antennas," IEEE J. Quant. Elec., vol. 24, pp. 255–260, 1988 and A. Nahata, D. H. Auston, T. F. Heinz, and C. Wu, "Coherent detection of freely propagating terahertz radiation by electro-optic sampling," Appl. Phys. Lett., vol. 68, pp. 150–153, 1996, both of which are hereby incorporated by reference. As a result, the temporal separation between pulses reflected from two closely separated surfaces can be determined directly from the time-domain waveform, without any need for temporal gating. In the previous work on reflection imaging with T-rays, as in OCT, the depth resolution was determined by the Rayleigh criterion. Two surfaces can only be distinguished if the distance between them is larger than $L_c/2$. Here, the factor of ½ arises from the two transits through the intervening medium of the pulse reflected from the farther surface. A depth resolution of ~100 microns was demonstrated using this simple time-of-flight imaging system. See Mittleman 1997. With single-beam time-of-flight techniques such as this, the only way to improve the depth resolution is to increase the bandwidth of the radiation, thereby decreasing $L_c$.

Methods of terahertz imaging, terahertz reflection imaging, terahertz near-field imaging, and terahertz gas sensing have all been patented within the last few years. See U.S. Pat. Nos. 5,623,145; 5,710,430; 5,789,750; 5,894,125; 5,939,721; and 6,078,047; each of which is incorporated herein by reference.

Given the interest in terahertz imaging and potential applications thereof, it is desirable to provide improvements that enhance the utility of these systems. In particular, terahertz systems with greatly enhanced depth resolution would prove advantageous for the semiconductor industry.

SUMMARY OF THE INVENTION

Accordingly, there is proposed herein a broadband system that provides greatly enhanced depth resolution through the use of phase shift interferometry. In one embodiment, the system comprises a transmitter, a beam splitter, a phase inverter, and a receiver. The transmitter provides a transmitted signal pulse that is split by the beam splitter into a measurement pulse and a reference pulse. The measurement pulse is applied to a sample, and a relative phase shift of approximately π radians is introduced between the measurement pulse and the reference pulse by the phase inverter. The measurement and reference pulses are then recombined to form a combined pulse that is detected by the receiver. The phase inverter may be a simple lens that introduces a Gouy phase shift by passing either the measurement or reference pulse through a focal point.

The phase inversion causes destructive interference in the combined pulse. This destructive interference is disrupted by perturbations of the measurement pulse by the sample. In this manner, a background-free measurement is provided. This provides a greatly enhanced sensitivity to small changes in the measurement waveform, regardless of the origin of these changes. This technique thus allows for measurements of time delays, changes in the frequency spectrum, and changes in attenuation. Various applications for this technique are described herein.

BRIEF DESCRIPTION OF THE DRAWINGS

A better understanding of the present invention can be obtained when the following detailed description of the preferred embodiment is considered in conjunction with the following drawings, in which:

FIG. 1 shows a graph of the frequency dependence of the Gouy phase shift under certain experimental conditions;

FIG. 2 shows a block diagram of a system that includes an optical measurement apparatus;

FIG. 3 shows a schematic of a preferred embodiment of a terahertz imaging system;

Figure 4:
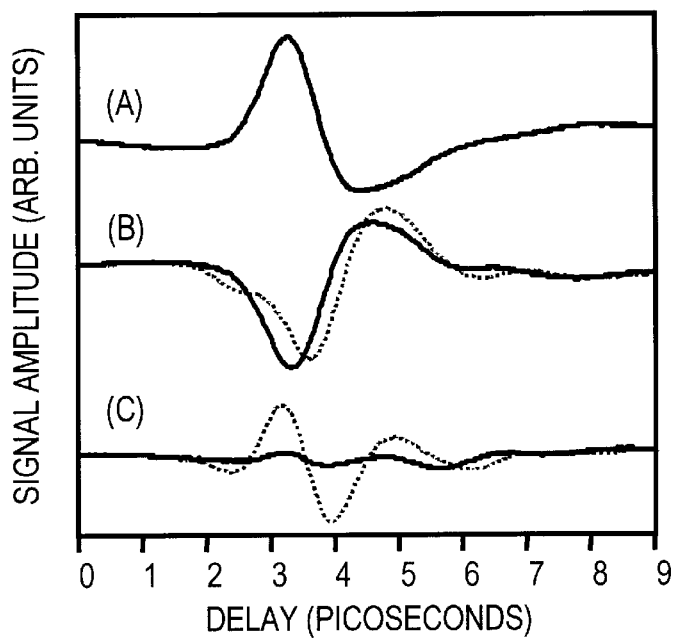
FIG. 4 shows sample waveforms to demonstrate interference arising from the Gouy phase shift.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENT

Gouy Phase Shift

Phase-sensitive interferometry has been recognized as a method for improving signal-to-noise in spectroscopic measurements (See F. V. Kowalski, W. T. Hill, and A. L. Schalow, "Saturated-interference spectroscopy," Opt. Lett., vol. 2, pp. 112–114, 1978; and M. D. Levenson and G. L. Eesley, "Polarization selective optical heterodyne detection for dramatically improved sensitivity in laser spectroscopy," Appl. Phys., vol. 19, pp. 1–17, 1979) and in imaging (See R. Oldfield, Light Microscopy: An illustrated Guide. London: Wolfe Publishing, pp. 95–103, 1994; and T. van Kessel and H. K. Wickramasinghe, "Measurement of trench depth by infrared interferometry," Opt. Lett., vol. 24, pp. 1702–1704, 1999). These methods depend on combining a narrow-bandwidth signal with a time-delayed version to achieve the desired interferometric measurement, and hence, they may not be suitable for the wide bandwidth signals that are normally encountered in terahertz time-domain spectroscopy systems.

Electromagnetic waves passing through a focus point are known to experience a phase shift. This phase shift is known as the Gouy phase shift, and for a Gaussian beam the additional phase (relative to a beam that is not focused) is calculated as follows:

$$\Delta\Phi_G(v) = \pi - 2\cdot\tan^{-1}\left(\frac{2v_c}{\pi v}\right), \qquad (1)$$

where v is the frequency and $v_c = fc/w_0^2$ is the "critical frequency", with f being the focal length of the lens, c being the speed of light, and $w_0$ being the beam waist before the lens. See A. B. Ruffin, J. V. Rudd, J. F. Whitaker, S. Feng, and H. G. Winful, "Direct observation of the Gouy phase shift with single-cycle terahertz pulses," Phy. Rev. Lett., vol. 83, pp. 3410–3413, 1999.

FIG. 1 shows the calculated phase shift as a function of frequency for two different critical frequencies. For frequencies larger than the critical frequency $v_c$, the Gouy phase shift approaches π, but for lower frequencies, the confocal parameter of the focusing beam approaches the focal length of the lens, and the phase shift rapidly drops to zero. For a typical experimental configuration, with a lens with f=13.2 cm, an estimated beam waist of 1.5 cm results in a critical frequency of $v_c$=176 GHz. The solid line in FIG. 1 shows the frequency-dependence of the phase difference ΔΦ for this critical frequency. The broken line shows the frequency dependence for optics offering a lower critical frequency.

Since this phase shift is approximately equal to π for the bulk of the frequency spectrum, it can be used to induce a destructive interference between two optical pulses. This provides a nearly background-free imaging mode and leads to a dramatic increase in the sensitivity to subtle features in a sample.

Physical System

FIG. 2 shows an interferometric imaging system with a computerized interface. The system includes a general purpose processor 10 coupled to a system memory 12. The system memory 12 may store software for processor 10 to execute, and may further store intermediate and final data gathered by the system. The processor 10 preferably relies on a digital signal processor (DSP) 14 to acquire measurements from the optical apparatus 100. In a preferred embodiment, the transmitter 16 repetitively creates femtosecond optical pulses which in turn create single-cycle picosecond pulses (T-rays) that pass through the measurement apparatus 100 to receiver 18, where they are detected and processed by DSP 14.

Receiver 18 preferably detects the waveform of the received T-rays. This may be accomplished through the use of well-known down-conversion techniques. One such technique employs a variable delay between the transmitted signal and the "opening of a gate" for the receive signal. By repeating (100 MHz is a typical repeat rate) the transmission and scanning the delay through the expected time of arrival for the T-ray at the receiver 18, the waveform can be measured by electronics operating at acoustic frequencies. The delay between the THz waveform and the detector gating pulse is scanned slowly at a rate of about 10 to 100 Hz. Thus, each sampling pulse samples the THz pulse at a somewhat different time, until the entire THz waveform has been reconstructed from the samples. This provides a "temporal down conversion" of the THz waveform into the kHz range, where it can readily be processed by electronics. The DSP 14 can then process the received waveform. The CPU 10 can then alter a measurement parameter, and cause the measurement to be repeated.

In the preferred embodiment, an object is placed in the measurement apparatus so that the CPU 10 can alter the position of the object relative to the optical path of the apparatus. The DSP 14 can thereby measure the received waveform as a function of object position, and can analyze the frequency dependence of the received waveform corresponding to each position of the object. A waveform for each pixel may be frequency analyzed in real time with by DSP 14 to extract compositional (or other) information. This information is preferably provided to the processor 10, which can then construct an image of the object that illustrates various physical properties. The image may be stored in memory 12 and shown to a user on a display device 20.

In general, many chemical compounds show very strong and highly specific frequency-dependent absorption and dispersion in the terahertz range. This is particularly true for gases, which have characteristic and narrow absorption lines in this range, but liquids and solids also have rather specific frequency-dependent absorption and dispersion characteristics in this frequency range, leading to characteristic time-domain waveforms when passing through different materials. One other possible property that is discussed further below is the measurement of separation between adjacent, dissimilar layers in the sample.

FIG. 3 shows a schematic of the optics for a preferred embodiment of an interferometric imager. This spectrometer shares many features with terahertz imaging systems described in B. Hu and M. C. Nuss, "Imaging with terahertz waves," Opt. Lett., vol. 20, pp. 1716–1719, 1995; and D. M. Mittleman, R. H. Jacobsen, and M. C. Nuss, "T-ray imaging," IEEE J. Sel. Top. Quant. Elec., vol. 2, pp. 679–692, 1996, both of which are hereby incorporated herein by reference. A transmitter 102 generates teraherz pulses which are formed into a primary (pulsed) beam by lens 104. The primary beam is directed to a beam splitter 106 which reflects a portion and transmits a portion of the primary beam.

One of the portions (the reflected portion in FIG. 3) forms a reference beam, while the other portion forms a measurement beam. Note that the reference arm and measurement arm may be switched without affecting the operation. The reference beam is retro-reflected from a movable mirror 110 and returns to the beam splitter 106. An optional path-bending mirror 108 may be provided in the reference arm to reduce the size of the apparatus.

The measurement beam is passed through a lens 112 that focuses the beam on a sample 114 near the focal point. The measurement beam reflects from the sample 114 and passes back through lens 112 to the beam splitter 106. The beam splitter 106 reflects a portion of the measurement beam and transmits a portion of the reference beam to form a result beam from the combination. A lens 116 focuses the result beam onto a receiver 118.

Using the technique of THz-TDS, a typical THz transmitter emits a single cycle of electro-magnetic radiation centered at 1 THz after being illuminated by a 100-femtosecond laser pulse from a modelocked laser. Because of the short duration of the THz-transient, the spectrum is broadband, typically extending from less than 100 GHz to several THz or more. Lenses 104, 112, and 116, are respectively used to collimate, focus, and collect the THz beam, which is arranged in a Michelson configuration for reflection imaging. Lenses 104, 112, and 116, are preferably composed of high-density polyethylene (for low reflection loss) or high-resistivity silicon (for broad-band achromaticity).

The beam splitter 106 may be a high-resistivity silicon wafer. This wafer is 0.5 cm thick, so that multiple reflections within the beam splitter are delayed by over 150 psec relative to the initial THz pulse, and are not measured. We note that this is not a 50/5 beam splitter—in fact, the transmitted THz field is reduced to 0.82 of the field incident on the silicon wafer, while the THz field reflected from the front surface of the wafer is reduced to 0.42. However, in the configuration shown, an ideal 50/50 split is not required, since both the sample arm and reference arm pulses experience one transmission and one front-surface reflection from the wafer. Thus, both fields are attenuated to ~0.35 by passing through the interferometer. The imbalance in the two arms is not significant because the interference occurs at the detector, after the two beams have been equalized. The achromaticity and low absorptivity of high-resistivity silicon are more important considerations in choosing a beam splitter material. See D. Grischkowsky, S. Keiding, M. van Exter, and C. Fattinger, "Far-infrared time-domain spectroscopy with terahertz beams of dielectrics and semiconductors," J. Opt. Soc. Am. B, vol. 7, pp. 2006–2015, 1990, which is hereby incorporated herein by reference.

A lens is placed in the sample arm of the interferometer, and the sample to be imaged is located on an X-Y table at its focus. For imaging, samples can be scanned transverse to the propagation direction of the THz beam so that an image is acquired pixel by pixel. See D. M. Mittleman, M. Gupta, R. Neelamani, R. G. Baraniuk, J. V. Rudd, and M. Koch, "Recent advances in terahertz imaging," Appl. Phys. B, vol.

68, pp. 1085–1094, 1999, which is hereby incorporated herein by reference. The beam in the second arm of the interferometer (the reference arm) is simply retro-reflected off of a flat mirror on a manual translation stage. The optical delays of the two arms are adjusted to be provide destructive interference in the result beam.

In addition to providing lateral spatial resolution for imaging, the lens also provides the phase shift which permits background-free imaging. The pulse 113 that passes through the focus acquires a Gouy phase shift to become pulse 115, while the phase of the pulse in the reference arm acquires no such additional phase shift. As previously mentioned, this phase shift is approximately π. Thus, when the pulses from the two arms of the interferometer reach the detector, they destructively interfere and a very small signal is measured. However, if the sample contains any feature that distorts either the amplitude or phase of the reflected THz pulse, this destructive interference is disrupted and a large signal is measured. In a sample containing multiple layers, the delay of the reference arm can be adjusted so as to cancel any one of the reflections from the sample, permitting a detailed study of any particular buried interface. Depending on the surface that is generating the reflection in the sample arm, it may be necessary to place an aperture or other attenuating means in the reference arm in order to adjust the relative amplitudes of the two pulses.

Analysis of Operational Principles

FIG. 4 shows several terahertz waveforms which illustrate this destructive interference. Curve (a) in FIG. 4 shows a waveform from the reference arm, while (solid) curve (b) shows a waveform from the measurement arm with a metal mirror placed in the focus of the imaging lens (the position normally occupied by the sample). These waveforms illustrate the nearly π phase shift acquired by the measurement beam relative to the reference beam. Solid curve (c) shows the strong destructive interference between these two pulses, resulting in a signal reduced in amplitude by more than 90%. When the measurement beam is delayed, as shown by the broken line in curve (b), the destructive interference is disturbed as shown by the broken line in curve (c).

Note that even with strong destructive interference, a small, low frequency remnant exists (solid curve (c)). This is because the Gouy phase shift does not provide a phase shift of π for all the wavelengths in the THz pulse. As a result, the interference between the sample and reference arms is not complete, particularly at low frequencies. The amplitude of the residual waveform depends on the parameters of the optical configuration such as the lens focal length (since this determines the critical frequency), and also on the bandwidth of the incident THz pulse.

Figure 5:
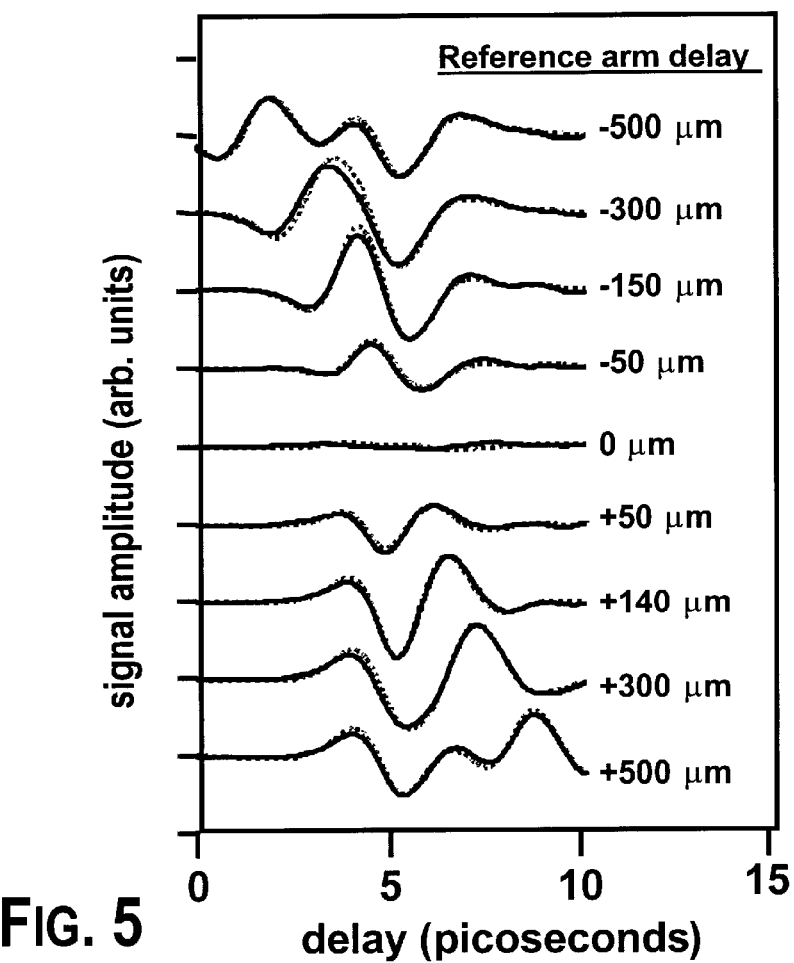
FIG. 5 shows a series of interfered waveforms for different lengths of the reference arm.

We can confirm that this incomplete cancellation is responsible for the observed waveforms by measuring the interfered waveforms as a function of the delay between the measurement and reference beams. For this measurement, both beams are retro-reflected with identical metal mirrors. In FIG. 5, we compare these measured waveforms (solid curves) with simulated waveforms (dashed curves). For these simulations, we measure the reference arm pulse, $E_{ref}(t)$, with the sample arm blocked. We then compute the sum of this reference pulse and a delayed, phase-shifted replica of itself. That is, we plot the inverse Fourier transform of:

$$E_{ref}(\omega)[1 + e^{-i2\omega D/c}e^{i\Delta\Phi_G(\omega)}] \quad (2)$$

for each displacement D of the reference arm mirror. Here, $E_{ref}(\omega)$ is the Fourier transform of $E_{ref}(t)$, and $\Delta\Phi(\omega)$ is the Gouy phase shift computed using the formula given earlier. This simulates the coherent superposition of the reference and sample arm waveforms, using only the reference arm waveform as an input. The excellent agreement between the measurements and simulations indicates that the Gouy phase is sufficient to explain the observed waveforms.

The use of interferometry affords several advantages in the detection of subtle features in a sample. First, the fractional change in peak-to-peak amplitude is much larger with interferometry. This provides an increased contrast in the imaging of dielectric discontinuities and also provides an enhanced sensitivity for the detection of sub-coherence-length layers (demonstrated further below). Interferometry also provides a background-free method for waveform acquisition, which naturally eliminates common-mode noise arising from laser fluctuations or other external perturbations. Unlike an interferometer for visible light, a THz interferometer does not require sub-micron stability, and is thus far less sensitive to vibrations. Finally, it is compatible with existing THz techniques, requiring only an additional thick silicon beam splitter and a mirror.

We note that previous THz imaging experiments have demonstrated a high degree of sensitivity to small shifts in the delay of a measured pulse. The interferometric technique converts these delay shifts into amplitude shifts, as follows. Consider one frequency component of frequency ω in the reference beam of the interferometer, which can be described as $E_R = e^{i\omega t}$. The corresponding component of the measurement arm waveform, with a φ phase shift, may be written as $E_S = -e^{i\omega t}e^{i\phi}$. Here, $\phi = 2D\lambda/c$ is the phase delay associated with the displacement of the reflecting surface in the sample arm, relative to zero optical path mismatch. We assume that D is much smaller than the confocal parameter of the focusing beam. The superposition of these two signals is $2i\sin(\phi/2)\cdot e^{i\omega t}e^{i\phi/2}$. In the limit of small displacement D, the amplitude of the interference signal is modulated by a factor of φ. Thus, small changes in the phase of the sample arm wave lead to equivalent small changes in the amplitude of the interfered wave.

Figure 6:
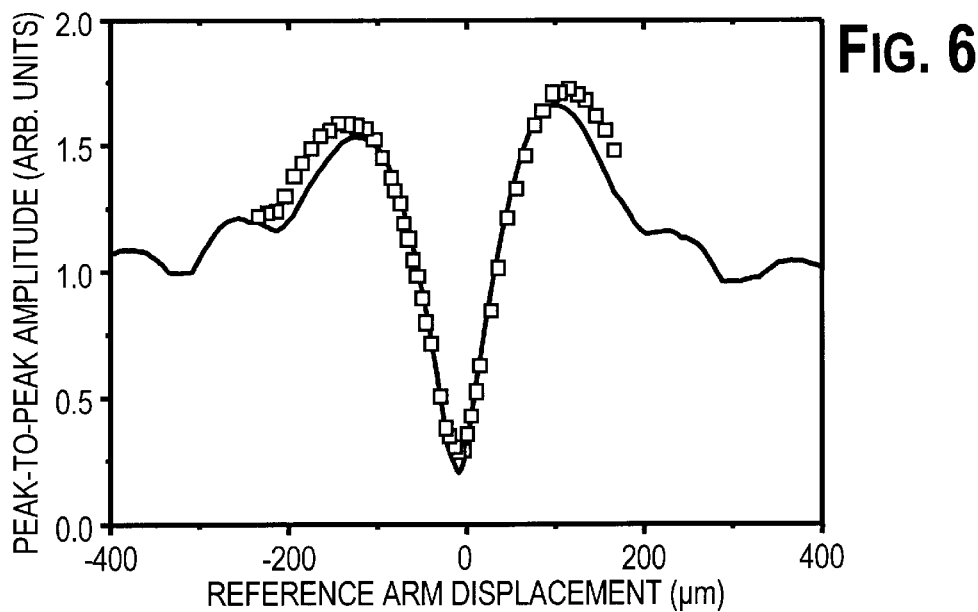
FIG. 6 shows the measured peak-to-peak amplitude of the received waveform for various delays.

FIG. 6 shows a simple metric for this single-cycle pulse interference effect. It displays the peak-to-peak amplitude of both the experimental and simulated waveforms as a function of the delay of the reference arm. This plot shows the destructive interference near zero delay, as well as constructive interference on either side of zero delay. The solid curve shows the peak-to-peak amplitudes of the simulated waveforms, calculated as described above with the measured reference arm waveform as an input. The open squares show experimentally determined results for this same quantity. For these measurements, the coherence length $L_c \sim 200$ μm and the critical frequency $v_c \sim 80$ GHz. Although the amplitude is not zero at zero delay, it is almost an order of magnitude less than at maximum constructive interference. Also, the amplitude variation is roughly contained within a displacement range of $D = \pm L_c/2$, and it is roughly proportional to D to within ~10 μm of its minimum value. This illustrates how interferometry provides a large dynamic range for the conversion of small shifts in delay into large amplitude variations.

Figure 7:
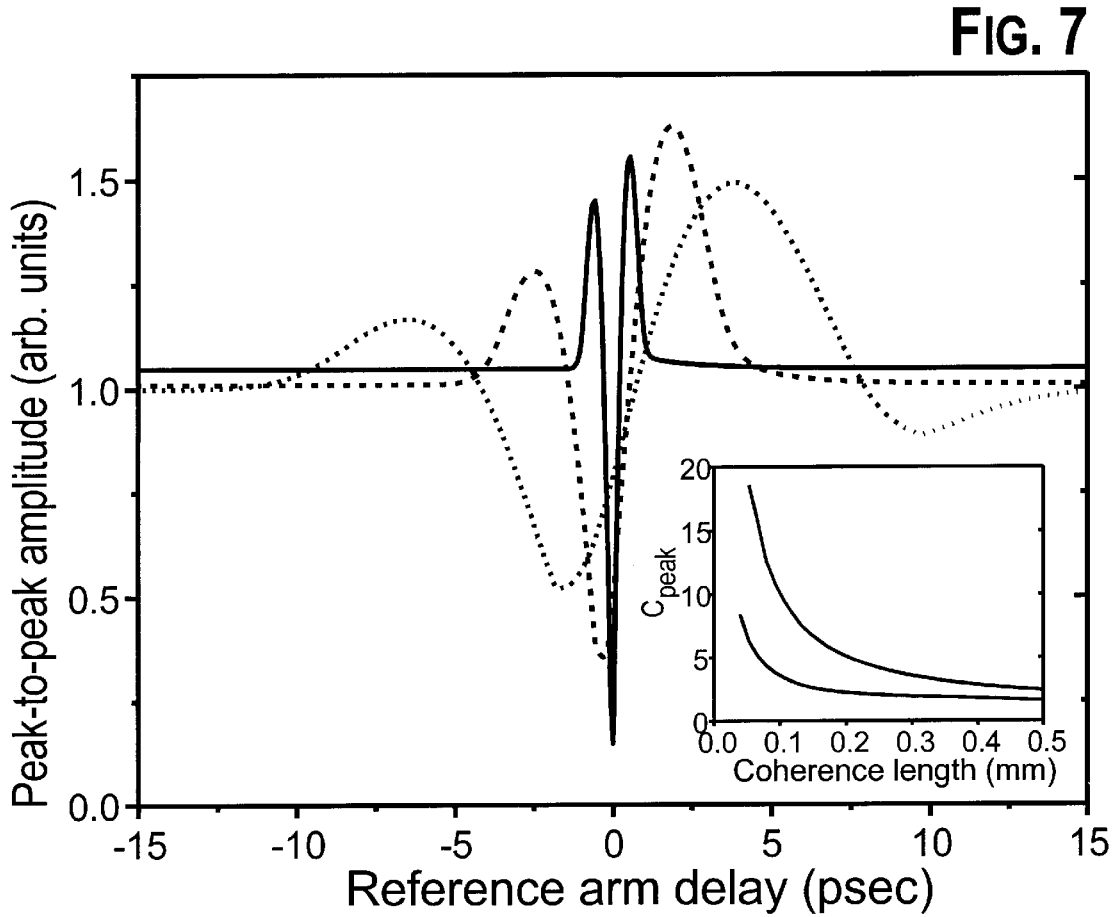
FIG. 7 shows the calculated peak-to-peak amplitude variation for different coherence lengths.

The behavior of the amplitude of the interfered waveform is further illustrated in FIG. 7, which shows a calculation of peak-to-peak waveform amplitude as a function of the reference arm delay, for three different pulse coherence lengths. These simulations use a model single-cycle pulse as an input (the first derivative of a Gaussian), and assume a critical frequency of $v_c = 0.1$ THz. With decreasing THz bandwidth, the optimal cancellation degrades, resulting in a smaller contrast between the minimum and maximum amplitudes. It is also interesting to note an increasing asymmetry relative to zero delay, which results from the increasingly severe (and asymmetric) distortion of the single-cycle pulse by the frequency-dependent Gouy phase.

To parameterize the degree of contrast enhancement, we define the peak contrast $C_{peak}$ as the ratio of the peak-to-peak amplitude at large displacement (when the two waveforms are well separated) to the minimum peak-to-peak amplitude (when the destructive interference is optimized). This provides a useful measure of the expected enhancement in both contrast and detectability. If the Gouy phase were exactly equal to $\pi$ at all frequencies, then the two waveforms would precisely cancel at D=0, and $C_{peak}$ would be infinite. The inset in FIG. 7 shows $C_{peak}$ as a function of the pulse coherence length for two different values of $v_c$. The upper curve is the result for $v_c$=100 GHz, while the lower curve is for $v_c$=300 GHz. It is clear that broader bandwidths (shorter coherence lengths) can significantly enhance the contrast. However, it is interesting to note that an order of magnitude contrast enhancement can be obtained with even a relatively modest bandwidth of ~1 THz, corresponding to a coherence length in free space of ~100 μm.

In order to quantitatively assess these improvements, it is necessary to compute the coherence length of the pulses used in the measurements. For the simulated pulses used to generate FIG. 8, this calculation is straightforward, but for experimentally generated pulses some subtleties arise. Normally, the coherence time $\tau_c$ of a light source is defined as the standard deviation of $|\Gamma^{(1)}(\tau)|^2$:

$$\tau_c^2 = \int (\tau - <\tau>)^2 |\Gamma^{(1)}(\tau)|^2 d\tau / \int |\Gamma^{(1)}(\tau)|^2 d\tau, \quad (3)$$

where $\Gamma^{(1)}(\tau)$ is the first-order coherence function:

$$\Gamma^{(1)}(\tau) = \int E(t-\tau) \cdot E(t) dt. \quad (4)$$

Since $\Gamma^{(1)}(\tau)$ is symmetric with respect to $\tau$, the average value $<\tau>$ in equation (3) vanishes.

Because $\Gamma^{(1)}(\omega)$ is the Fourier transform of the power spectrum, one may formulate an alternative definition for $\tau_c$ in terms of the spectral bandwidth:

$$\tau_c = \frac{1}{\pi \cdot \Delta v} \quad (5)$$

where $\Delta v$ is the full-width at 1/e of the power spectrum. Once the coherence time is determined, the coherence length is computed using $L_c = c\tau_c/n$, where n is the refractive index of the medium in which the radiation propagates. See O. Svelto, Principles of Lasers, 4th ed. New York: Plenum Press, 1998.

In many cases, these two formulations are equivalent. However, in the case of interest here, a typical THz pulse consists not only of a single-cycle oscillation, but also of a subsequent train of smaller oscillations. This temporal structure is entirely repeatable, and is not due to noise in the measurement. Rather, it can arise from the effects of water vapor absorption in the THz beam path, or from temporal echoes arising from either optical or electrical reflections in the transmitter or receiver antenna. See M. van Exter, C. Fattinger, and D. Grischkowsky, "Terahertz time-domain spectroscopy of water vapor," Opt. Lett., vol. 14, pp. 1128–1130, 1989. In either case, the presence of this structure following the main THz pulse mimics the effect of a narrow-band component within the pulse spectrum. As a result, the coherence time as calculated by Eqn (3) is artificially lengthened if this extended temporal structure is included in the computation.

Figure 8:
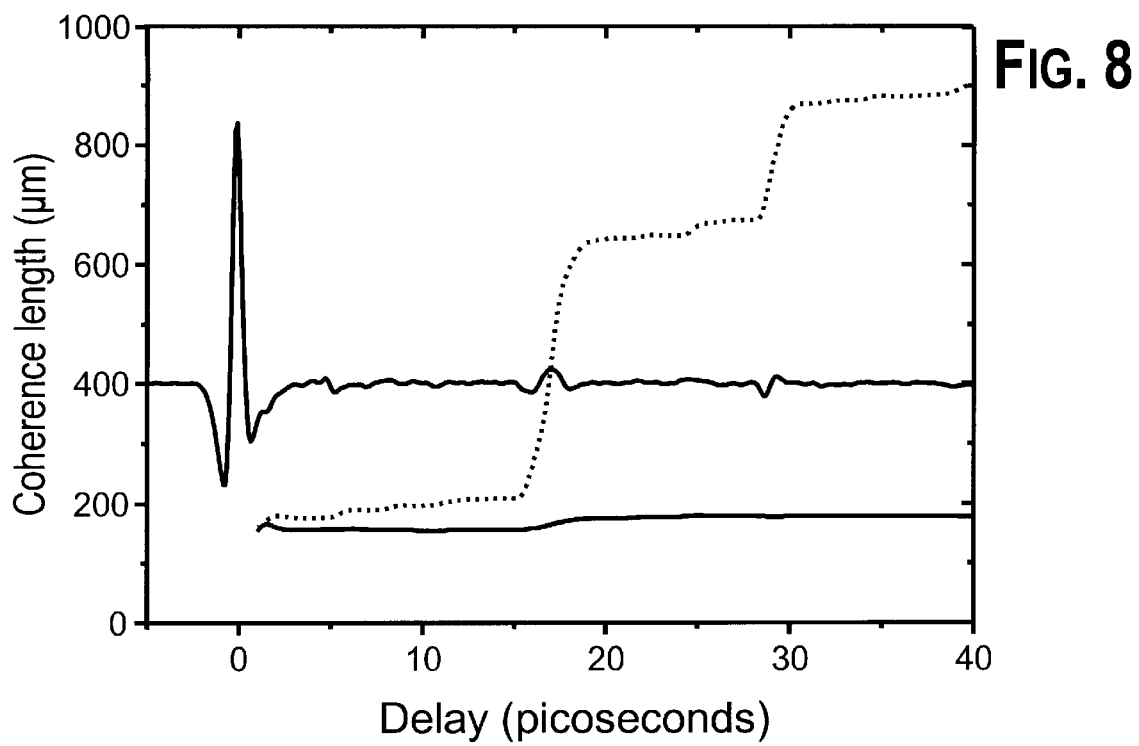
FIG. 8 shows an analysis of two coherence length calculation methods.

This is demonstrated in FIG. 8, which shows a typical THz waveform along with the coherence length calculated using the two methods outlined above. This waveform has been measured within a purged container, so that the effects of water vapor are minimized; even so, considerable structure follows the main pulse. In the calculation of the coherence length, this time-domain waveform is numerically truncated using a square window function with tapered rising and falling edges, and the coherence length is calculated as a function of the location of the falling edge of the window. The rising edge is kept fixed at D=−5 psec, well before the beginning of the pulse. The dashed line, calculated with the method of equations (3) and (4), shows a large increase in the computed coherence length each time the window function broadens to encompass one of the small echoes that follow the main pulse. The coherence length calculated using the full waveform is 900 μm, nearly six times larger than the value calculated with only the initial single-cycle transient.

In contrast, since the small structures at large values of the delay do not dramatically change the shape of the spectrum, the value of $L_c$ calculated using equation (5) (shown in FIG. 8 as a solid line) is much less sensitive to the width of the window function. Of course, the coherence properties of the radiation necessarily include the full time dependence of the THz electric field, and are correctly characterized using equations (3) and (4), along with higher order coherence functions. However, for the purposes of determining the depth resolution in time-of-flight measurements such as the ones described here, only the coherence of the initial portion of the waveform is relevant. In order to accurately extract a measure of the limits in such imaging experiments, the inverse spectral bandwidth is a more reliable measure than the width of $\Gamma^{(1)}(\tau)$. The relevant coherence length can be defined to be the limiting value as the width of the window function shrinks to include only the initial transient.

Figure 9:
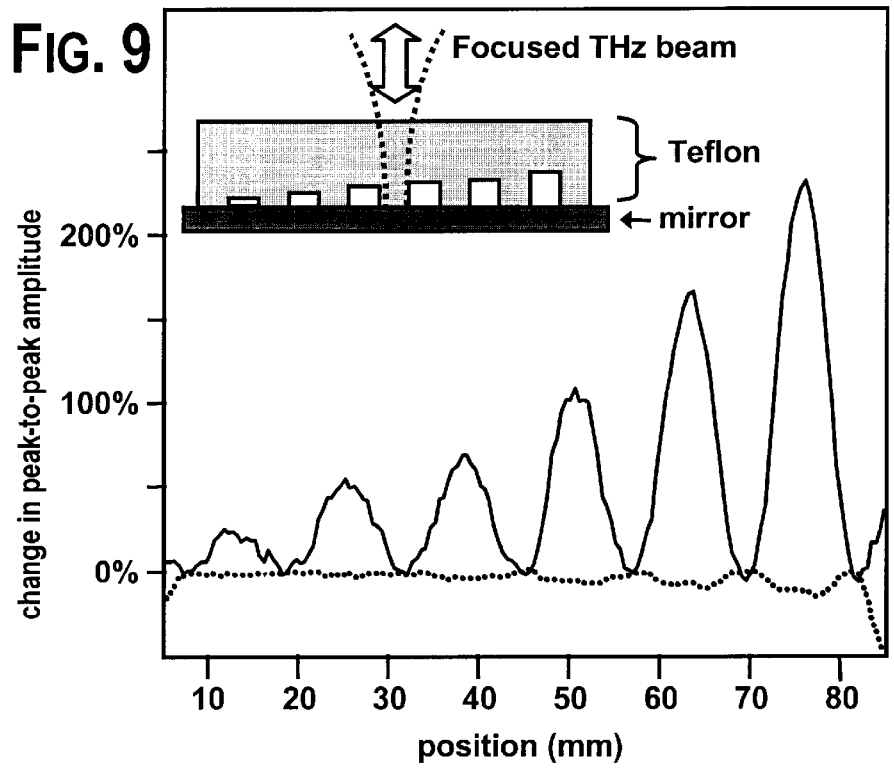
FIG. 9 shows experimental results of a line scan of an interface between sample layers.

To demonstrate the ability to image below the coherence limit, we have constructed several model samples containing thin, well-controlled features. The inset on FIG. 9 shows a schematic of one Teflon-metal model, with air gaps between the two pieces ranging from 12.5 μm to 100 μm in width. This model is positioned so that the metal-plastic interface is located at the focus of the imaging lens in the sample arm. We carefully adjust the tilt of the sample so that, as it is scanned transverse to the beam propagation direction, the distance from the lens to this interface does not vary. We image a line scan across this sample, and compare the results with and without the interferometric cancellation.

FIG. 9 shows the percent change in the peak-to-peak amplitude of the measured waveform relative to a waveform measured at a position on the sample containing no air gap. For these measurements, the delay of the reference arm has been used to optimize the cancellation of the pulse reflected from the metal-teflon interface, with no air gap in the beam. FIG. 9 compares the interferometric measurement (solid line) with the non-interferometric measurement (broken line). Note that the waveform increases in amplitude when interferometry is employed, but decreases when it is not. The contrast of the interferometric signal is enhanced by more than an order of magnitude over the non-interferometric signal. In the interferometric mode, the areas with no air gap show strong destructive interference. The change in the cancellation when an air gap is encountered results in a large increase in the amplitude of the measured waveform. As a result, it is possible to easily detect the smallest air gap using the interference effect. This 12.5 μm gap is roughly 25 times smaller than the coherence length of the terahertz pulses used to collect this data.

As one would expect, the degree of modulation depends on the bandwidth of the THz pulse used to collect the data. As the bandwidth is decreased, the sensitivity also decreases. Also, if the bandwidth is broad enough, then the variation in peak-to-peak amplitude is nearly linear with the gap width, but for narrower bandwidth pulses, the variation departs from linearity. These results are consistent with the simulations shown in FIG. 7, in which longer coherence lengths lead to reduced contrasts.

Figure 10:
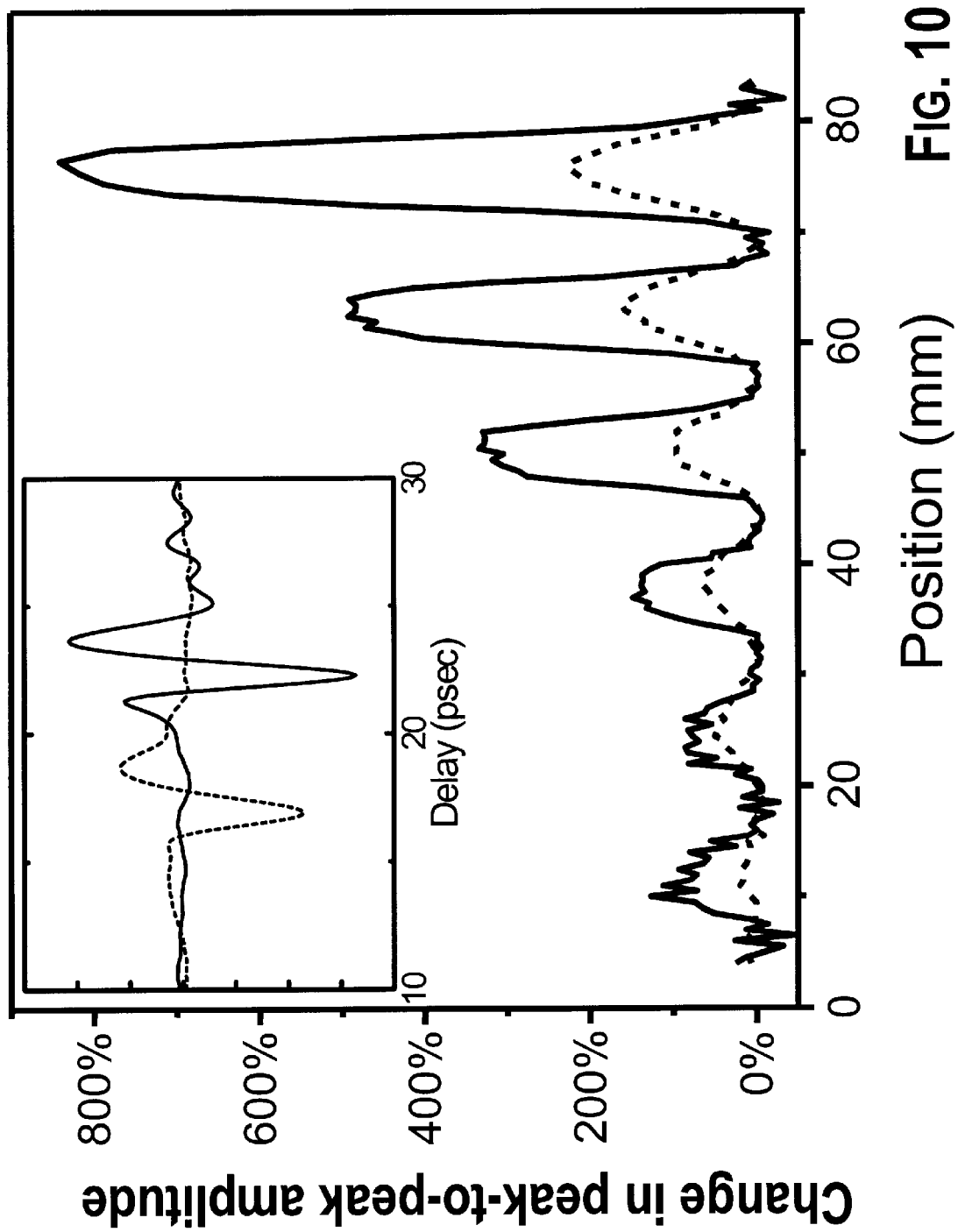
FIG. 10 compares experimental results for different coherence lengths.

Ordinarily, one would expect the depth resolution in a time-of-flight measurement to be determined by the bandwidth of the radiation, and to be only weakly dependent on its central frequency. For example, for a light source with a Gaussian spectrum, the coherence time is simply $\frac{1}{4\pi\sigma_v}$, where $\sigma_v$ is the standard deviation of the squared power spectrum. However, because of the frequency dependence of the Gouy phase, the center frequency can also play a role in these measurements. FIG. 10 shows two line scans, both representing the peak-to-peak amplitudes of the interfered waveforms. Different sets of THz antennas have been used to collect these two scans. The inset shows the two different reference arm waveforms used to acquire these two line scans. These two pulses have comparable bandwidths and therefore coherence lengths, but the spectrum-weighted mean frequency of the solid curve is ~40% larger than that of the dashed curve. Because the central frequency is shifted to higher values, the Gouy phase difference is closer to $\pi$ for most of the frequency content of this waveform, so the destructive interference between sample and reference pulses is more effective. As a result, even though the coherence lengths are quite similar, the pulse with a higher average frequency gives a substantially enhanced contrast in imaging the sample. Using the waveform with the higher central frequency, we observe that the waveform nearly doubles in amplitude in the vicinity of the smallest, 12.5 $\mu$m gap.

The role of the transverse spatial resolution in these data should also be noted. The features shown in the sample of FIG. 9 are all much thinner than the Rayleigh range of the focused THz beam, even for its highest frequency components, so it is reasonable to neglect wavefront curvature in these experiments. This effectively decouples the considerations of transverse and longitudinal resolution in an imaging measurement. However, it is important to remember that different frequency components focus to different spot sizes, so the focal spot of this broadband light source is quite complicated. Since we are relying on a time-domain metric (the peak-to-peak amplitude of the temporal waveform) for formation of images, the expected transverse resolution is not so easy to determine. One might guess that it would vary approximately linearly with the central frequency of the radiation. We extract from the data of FIG. 10 a 10%-to-90% rise for the largest air gap, as a measure of the transverse spatial resolution. We find that the data acquired using the waveform with a higher central frequency gives a transverse resolution of ~2.5 mm, while the lower frequency result is ~3.8 mm, in rough proportion to the shift in the central frequency of the THz pulse. We note that the interferometric technique permits the resolution of features in the longitudinal direction that are more than 100 times smaller than the smallest features that can be resolved in the transverse dimensions.

Methods of Application

In a first example of an application method, the system of FIGS. 2–3 is used to measure the delamination of layers in a semiconductor package. When correctly laminated, the interface between the layers produces a single reflection, whereas a gap formed by delamination will produce a reflection from each side of the gap. The semiconductor package is placed on the sample table and aligned so that the interface of interest will traverse perpendicularly to the incident beam. In an alternate embodiment, the CPU 10 may employ feedback control to position the sample table (or lens 112) along the beam axis to keep the interface at the focus.

The mirror 110 is positioned (either manually or under control of CPU 10) so that the reference beam destructively interferes with the reflection from the interface of interest. An aperture or other attenuation mechanism may be placed in the reference path to make the destructive interference as complete as possible.

As the sample table is scanned through its X-Y motions, the DSP 14 gathers waveform amplitude measurements for each pixel. Any delamination will cause the measured amplitudes to increase in proportion with the size of the gap (for small gaps). Larger gaps may be measured from the time delay of the reflection. The processor 10 may construct a cross-sectional image of the semiconductor package, using intensities or colors to represent the degree of measured delamination. This image is then shown to the user. Alternatively, the processor 10 may simply collect statistics for quality control, and forward them for use elsewhere in a larger system.

Alternative Embodiments

Figure 11:
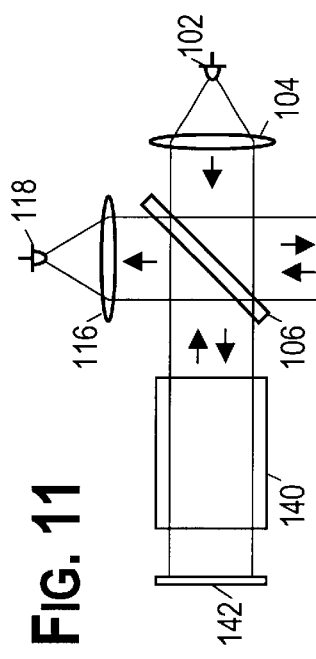
FIG. 11 shows an alternative embodiment for measuring gas compositions.

An example of an alternative embodiment which may be used for high sensitivity trace gas detection and analysis is shown in FIG. 11. In this embodiment, the transmitter 102 transmits a pulse through collimating lens 104. A portion of the pulse energy is reflected from the beam splitter 106 and enters the reference arm. This reference pulse is focused by lens 112 and retro-reflected by mirror 110. We note that the lens, which provides the Gouy phase shift and therefore the destructive interference, has been moved from the measurement arm of the interferometer to the reference arm. Since only the difference in the acquired phases of the two arms is relevant, the lens can be placed in either arm, particularly if transverse spatial resolution of the sample is not required. However, unlike in the previously described embodiment in which mirror 110 was moveable, in this embodiment both the mirror 110 and the lens 112 are jointly moveable. A preferred embodiment is to mount both the mirror 110 and the lens 112 on a single translatable stage, so that they may be moved as a unit while the distance between them remains fixed.

A portion of the pulse energy from the transmitter is also transmitted through the beam splitter 106, and then passes through a region 140 containing a trace gas or gas mixture to be sensed. In one embodiment, this region consists of a gas cell with high-density polyethylene windows which transmit the THz pulse but which contain the gaseous sample within the cell. The THz pulse retro-reflects off of mirror 142 and then passes a second time through the region 140.

The beam splitter 106 recombines the pulses from the reference and measurement arms and directs the combined pulse to a measurement apparatus consisting of a focusing lens 116 and a receiver antenna 118.

If the region 140 contains no gas with a THz absorption signature, then the measurement and reference pulses will be out of phase according to the Gouy phase shift described above, and a minimal waveform will be measured. However, if there is a gas in the region 402 which has one or more absorption lines within the bandwidth of the THz pulse, the absorption of this gas will alter the THz pulse which traversed the measurement arm, and the destructive interference will be disrupted as a result. It is anticipated that this will lead to a significant increase in the ability to detect small quantities of certain gases.

Figure 12:
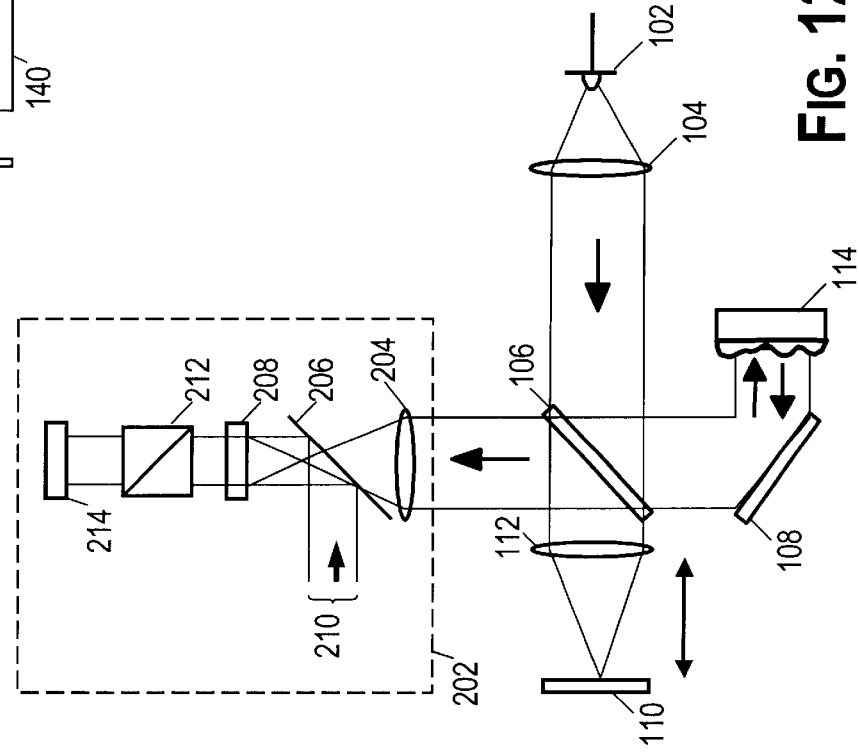
FIG. 12 shows an alternative embodiment in which the image is captured rather than constructed pixel by pixel.

An example of an alternative embodiment which may be used for delamination measurement is shown in FIG. 12. In this system, an entire image is measured simultaneously rather than pixel-by-pixel. In this embodiment, the transmitter 102 transmits a pulse through collimating lens 104. A portion of the pulse energy reflects from beam splitter 106 and enters the measurement arm. This measurement pulse reflects from a sample 114 and returns to the beam splitter 106. An optional, path-bending mirror 108 is also shown in the measurement arm.

A portion of the pulse energy from the transmitter also passes through the beam splitter 106 into the reference arm. This reference pulse passes through a focusing lens 112, reflects off a mirror 110 at the focal point, and returns through lens 112 to the beam splitter 106. The reference pulse has acquired an additional phase shift (the Gouy phase shift) relative to the measurement beam due to its passage through the focus.

The beam splitter 106 recombines the measurement and reference pulses and directs the combined pulse to a measurement apparatus 202. In one embodiment, the measurement apparatus is modeled after the apparatus of Z. Lu, P. Campbell, and X.-C. Zhang, Applied Physics Letters, volume 71, no. 5, pp. 593–596 (1997), which is hereby incorporated by reference. The apparatus 202 includes an objective lens 204 which casts an image of the combined pulse through a pellicle 206 onto an electro-optic crystal 208. A polarized optical beam 210 in the visible range is reflected from the pellicle 206 and travels through the electro-optic crystal 208 with the combined pulse. The crystal 208 causes an interaction of these beams that essentially transfers the information from the combined pulse to the optical beam 210. The optical beam 210 then travels through a polarizer 212 that is oriented to block the optical beam 210. However, if the optical beam has interacted with a THz pulse in the electro-optic crystal 208, then its polarization will be rotated, and a portion of the optical beam will pass through the polarizer 212. By measuring this transmitted component, the amplitude of the THz pulse can be determined. If a sufficiently large electro-optic crystal and optical beam are employed, then the entire wavefront of the THz beam can be sensed in parallel, using a CCD (charge-coupled device) camera 214. The image is processed to determine the intensity information originally carried by the combined pulse, and hence the delamination measurements.

Figure 13:
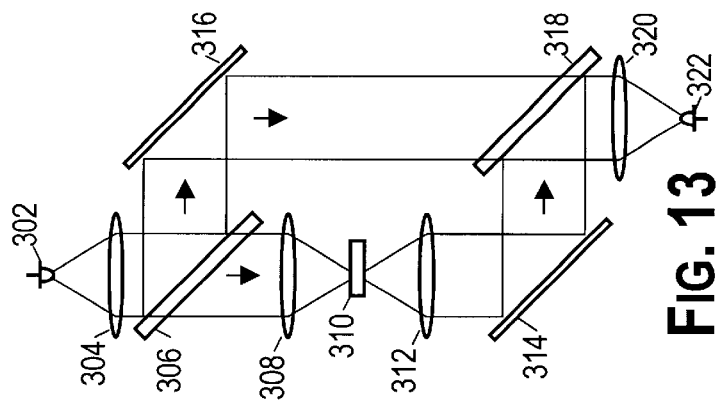
FIG. 13 shows another alternative embodiment for transmissive measurement of the sample.

FIG. 13 shows an embodiment that may be employed to measure compositional information. A transmitter 302 produces T-rays that pass through collimating lens 304 to a beam splitter 306, which produces a measurement T-ray and a reference T-ray. The measurement T-ray passes through a focusing lens 308 that focuses the T-ray on a sample 310. (Sample 310 may be gaseous, liquid, or solid.) The T-ray passes through sample 310 to a collimating lens 312, which directs the measurement T-ray off a mirror 314 to a second beam splitter 318.

The reference T-ray from beam splitter 306 reflects off a mirror 316 and travels to second beam splitter 318. The beam splitter 318 combines the measurement and reference T-rays, and passes the combined T-ray through a gathering lens 320 to receiver 322. The DSP 14 measures the waveform of the combined T-ray and may perform a spectral analysis to determine the composition of the sample 310.

To do a proper analysis, the DSP 14 is preferably calibrated with the measurement path blocked. This allows the DSP to determine the spectral content of the transmitted T-rays. The measurement path is then unblocked, and the measurement and reference T-rays destructively interfere. Any spectral change caused to the measurement T-ray by the sample will be made apparent by the lack of destructive interference at that frequency.

The disclosed system is capable of operation at any frequency where received waveforms can be measured. Currently, feasible operation exists at terahertz frequencies (e.g. between about 10 GHz and about 100 THz) and below, and technological advances are expected to make higher frequency operation feasible as well. In one contemplated alternative embodiment, single-cycle microwave pulses are employed.

The disclosed system operates best using wideband pulse signals, which provides a shorter coherence length and hence higher depth resolution. For the sake of a convenient definition, broadband signal is hereby defined to be a signal having a bandwidth that is greater than or equal to 50% of its central frequency.

The above described systems rely on a lens as a phase inverter, but inversion techniques other than the Gouy phase shift may be employed. For example, at microwave frequencies, a phase inverter may record the transmitted waveform, invert it electronically, and re-transmit. Any methods for a substantially uniform phase shift of $\pi$ may be employed in realizing the present invention.

Other embodiments include other transmissive and reflective interferometric configurations. Many such interferometric configurations are described in chapter 7 of Born and Wolf, Principles of Optics, $7^{th}$ ed., @1999, Cambridge University Press, Cambridge.

Advantages

The disclosed invention potentially offers numerous advantages, including resolution below the Raleigh limit in a time-of-flight imaging system. The alternative way to achieve enhanced depth resolution is to use radiation with broader bandwidth. In our experiments, the resolution is determined by the optical components, which limit the spectral range over which the 180 degree Gouy phase is imposed on the focusing beam. Better optics would lead to better depth resolution, and better optics are far easier to obtain than broader bandwidths.

Another potential advantage is the substantially enhanced sensitivity. Destructive interference makes the measurement "background free", meaning that any measured signal is directly attributable to the quantity of interest and does not include a bias. Because such measurements are better able to use available dynamic range and do not suffer from common-mode noise, enhanced sensitivity results.

Other advantages offered by THz time-domain systems, include a signal-to-noise ratios of 10,000 to one, no requirement for cooled detectors, compact construction, and transmitter/receiver technology that is compatible with integrated circuit technology.

Numerous variations and modifications will become apparent to those skilled in the art once the above disclosure is fully appreciated. It is intended that the following claims be interpreted to embrace all such variations and modifications.

What is claimed is:

1. A measurement apparatus that comprises:
   a transmitter that provides a transmitted signal pulse;
   a beam splitter that splits the transmitted signal pulse into a measurement pulse and a reference pulse, wherein the measurement pulse interacts with a sample before being re-combined with the reference pulse to form a combined pulse;

a phase inverter that provides a relative phase shift between the measurement and reference pulses of approximately π radians across most frequency components of the transmitted pulse; and a receiver that receives the combined pulse.

2. The apparatus of claim 1, wherein the transmitted signal pulse has a bandwidth that is greater than 50% of the transmitted signal pulse's central frequency.

3. The apparatus of claim 2, wherein the transmitted signal pulse has a central frequency greater than 10 GHz and less than 100 THz.

4. The apparatus of claim 2, wherein the phase inverter includes a lens that imposes a Gouy phase shift on only one of the measurement or reference pulses.

5. The apparatus of claim 4, wherein the phase inverter focuses the measurement pulse at a sample point.

6. The apparatus of claim 5,
wherein the phase inverter further collimates the measurement pulse as the measurement pulse reflects from the sample point and directs the reflected measurement pulse to the beam splitter,
wherein the reference pulse is retro-reflected from a mirror and returns to the beam splitter, and
wherein the measurement pulse and reference pulse are re-combined at the beam splitter to form the combined pulse.

7. The apparatus of claim 4,
wherein the phase inverter focuses the reference pulse on a retro-reflective mirror and collimates the reference pulse as the reference pulse reflects from the mirror,
wherein the measurement pulse is applied to the sample, and
wherein the measurement pulse and reference pulse are re-combined at the beam splitter to form the combined pulse.

8. The apparatus of claim 5, further comprising:
a collimating lens that receives the measurement pulse after the measurement pulse passes through the sample; and
a set of mirrors that direct the measurement pulse from the collimating lens and the reference pulse from the beam splitter to a second beam splitter where the pulses are re-combined to form the combined pulse.

9. The apparatus of claim 1, wherein the receiver includes a time gate, wherein the apparatus includes a scanning mirror that alters a time delay between transmission of the signal pulse and opening of the time gate, and wherein the apparatus is coupled to a controller that determines a waveform of the combined pulse from a series of combined pulses.

10. The apparatus of claim 9, wherein the controller processes the waveform to determine a parameter of interest for each of multiple sample points.

11. The apparatus of claim 10, wherein the parameter of interest is sample composition.

12. The apparatus of claim 10, wherein the parameter of interest is separation between two dissimilar layers of the sample.

13. The apparatus of claim 9, wherein the parameter of interest is a concentration value of one or more gases.

14. A method of determining a sample property, wherein the method comprises:
generating an electromagnetic pulse;
splitting the electromagnetic pulse into a measurement pulse and a reference pulse;
applying the measurement pulse to a sample;
introducing a relative phase shift between the measurement pulse and a reference pulse of approximately pi radians; and
re-combining the measurement pulse with the reference pulse to form a combined pulse.

15. The method of claim 14, wherein said introducing a relative phase shift includes:
passing the measurement pulse through a first number of focal points, said first number being zero or more;
passing the reference pulse through a second number of focal points, said second number being zero or more,
wherein said first and second numbers differ by an odd number.

16. The method of claim 14, further comprising:
measuring an amplitude of the combined pulse.

17. The method of claim 14, further comprising:
measuring a waveform of the combined pulse.

18. The method of claim 16, further comprising:
processing the waveform to determine a property of the sample.

19. A system that comprises:
an optical means for generating electromagnetic pulses, splitting the pulses into measurement pulses and reference pulses, applying the measurement pulses to a sample, introducing an approximate phase inversion between the measurement and reference pulses, recombining the measurement and reference pulses into combined pulses, and measuring the waveform of the combined pulses;
a controller means for processing the waveform of the combined pulses to determine a sample property;
a computer means for generating an image indicative of the sample property; and
a display means for communicating the image to a user.

20. The system of claim 19, wherein the electromagnetic pulses have a duration of less than ten picoseconds.

21. The system of claim 19, wherein the electromagnetic pulses have a center frequency in the microwave region.

22. The system of claim 19, wherein the sample property is separation at a layer interface.

23. The system of claim 19, wherein the sample property is chemical composition.

24. The system of claim 19, wherein the sample property is a concentration value of one or more gases.

* * * * *

UNITED STATES PATENT AND TRADEMARK OFFICE
CERTIFICATE OF CORRECTION

PATENT NO. : 6,665,075 B2
DATED : December 16, 2003
INVENTOR(S) : Mittleman et al.

It is certified that error appears in the above-identified patent and that said Letters Patent is hereby corrected as shown below:

Title page,
Item [73], Assignee, please add:
-- [73]  Assignee:   WM. Marsh Rice University, Houston, TX (US) --

Signed and Sealed this

Sixteenth Day of March, 2004

JON W. DUDAS
*Acting Director of the United States Patent and Trademark Office*